(12) United States Patent
Champseix et al.

(10) Patent No.: US 7,377,189 B2
(45) Date of Patent: May 27, 2008

(54) SAMPLING DEVICE AND METHOD FOR AN AUTOMATIC ANALYSER

(75) Inventors: Serge Champseix, Tarnac (FR); Henri Champseix, Saint Gely du Fesc (FR)

(73) Assignee: C2 Diagnostics, Montpellier Cedex (FR)

( * ) Notice: Subject to any disclaimer, the term of this patent is extended or adjusted under 35 U.S.C. 154(b) by 9 days.

(21) Appl. No.: 10/561,242

(22) PCT Filed: Jul. 16, 2004

(86) PCT No.: PCT/FR2004/001872

§ 371 (c)(1),
(2), (4) Date: Dec. 19, 2005

(87) PCT Pub. No.: WO2005/010497

PCT Pub. Date: Feb. 3, 2005

(65) Prior Publication Data

US 2007/0095159 A1    May 3, 2007

(30) Foreign Application Priority Data

Jul. 18, 2003    (FR) .................................. 03 08766

(51) Int. Cl.
 *B01L 3/02*    (2006.01)
(52) U.S. Cl. ............................. 73/864.25; 73/864.01; 73/864.24; 422/99; 422/100; D24/128
(58) Field of Classification Search ................. 73/863, 73/863.31–863.33, 864, 864.25; 422/63–66; 604/411–413; D24/127–130
See application file for complete search history.

(56) References Cited

U.S. PATENT DOCUMENTS

| | | | | |
|---|---|---|---|---|
| 3,552,212 | A | * | 1/1971 | Ohlin ....................... 73/864.22 |
| 3,748,907 | A | * | 7/1973 | Sahmel ..................... 73/864.24 |
| 3,748,911 | A | * | 7/1973 | Rousselet et al. ......... 73/864.22 |
| 3,858,450 | A | * | 1/1975 | Jones ....................... 73/863.72 |
| 3,949,615 | A | * | 4/1976 | Stein et al. .............. 73/864.22 |
| 4,000,973 | A | * | 1/1977 | Petersen ....................... 436/54 |
| 4,076,503 | A | * | 2/1978 | Atwood et al. ............. 422/100 |
| 4,343,766 | A | * | 8/1982 | Sisti et al. .................... 422/63 |
| 4,434,672 | A | * | 3/1984 | Williamson et al. ..... 73/864.22 |
| 4,499,053 | A | * | 2/1985 | Jones ......................... 422/68.1 |
| 4,570,495 | A | * | 2/1986 | Terada ..................... 73/864.25 |
| 4,766,082 | A | * | 8/1988 | Marteau D'Autry ........ 436/178 |
| 4,869,114 | A | * | 9/1989 | Kido et al. .............. 73/864.24 |
| 4,927,603 | A | * | 5/1990 | Fischer et al. ................. 422/67 |
| 4,951,512 | A | * | 8/1990 | Mazza et al. ............. 73/864.23 |
| 5,032,361 | A | * | 7/1991 | Kleinhappl et al. ........... 422/67 |
| 5,525,298 | A | * | 6/1996 | Anami ........................ 422/63 |
| 5,744,729 | A | * | 4/1998 | Tanaka ..................... 73/864.25 |
| 5,756,905 | A | * | 5/1998 | Ueda ....................... 73/864.24 |
| 6,447,728 | B1 | * | 9/2002 | Wilmes et al. .............. 422/100 |

(Continued)

FOREIGN PATENT DOCUMENTS

SU    1583836    8/1990

*Primary Examiner*—Hezron Williams
*Assistant Examiner*—David A. Rogers
(74) *Attorney, Agent, or Firm*—Young & Thompson

(57) ABSTRACT

A method and device for an automatic analyzer, in particular for blood analysis sampling consists in displacing a sampling needle (5) rotatable around an axis (X2) which forms an angle with the sampling needle. The method and device are particularly suitable for use in a small blood sampling automate.

24 Claims, 2 Drawing Sheets

U.S. PATENT DOCUMENTS 6,866,820 B1 * 3/2005 Otto et al. .................... 422/63
6,913,934 B2 * 7/2005 Dales et al. ................. 436/180
7,127,957 B2 * 10/2006 Mathur et al. ........... 73/864.81
7,186,384 B2 * 3/2007 Ruther et al. ................ 422/103
2002/0064886 A1 * 5/2002 Nakagawa et al. ......... 436/177

* cited by examiner

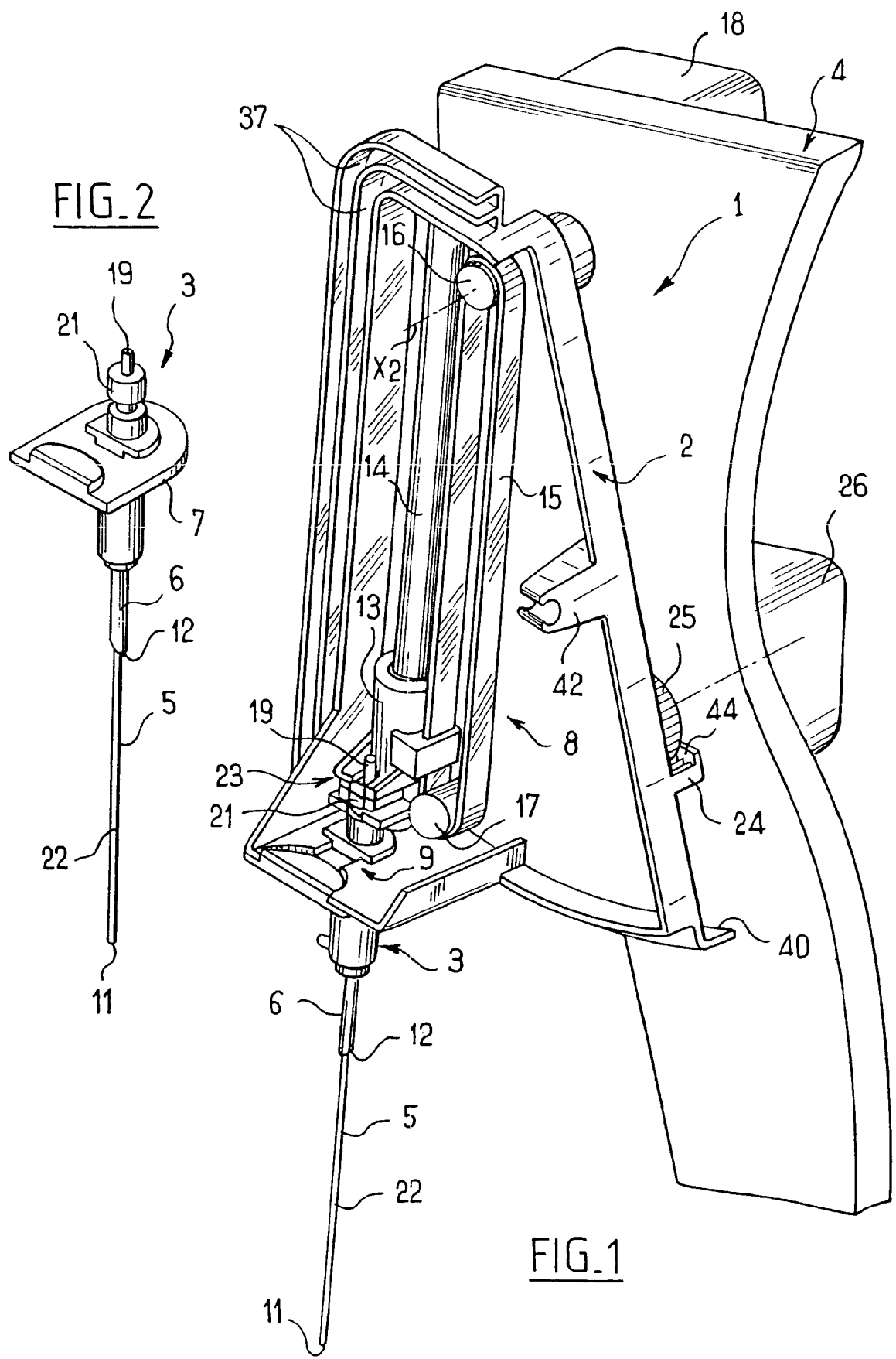

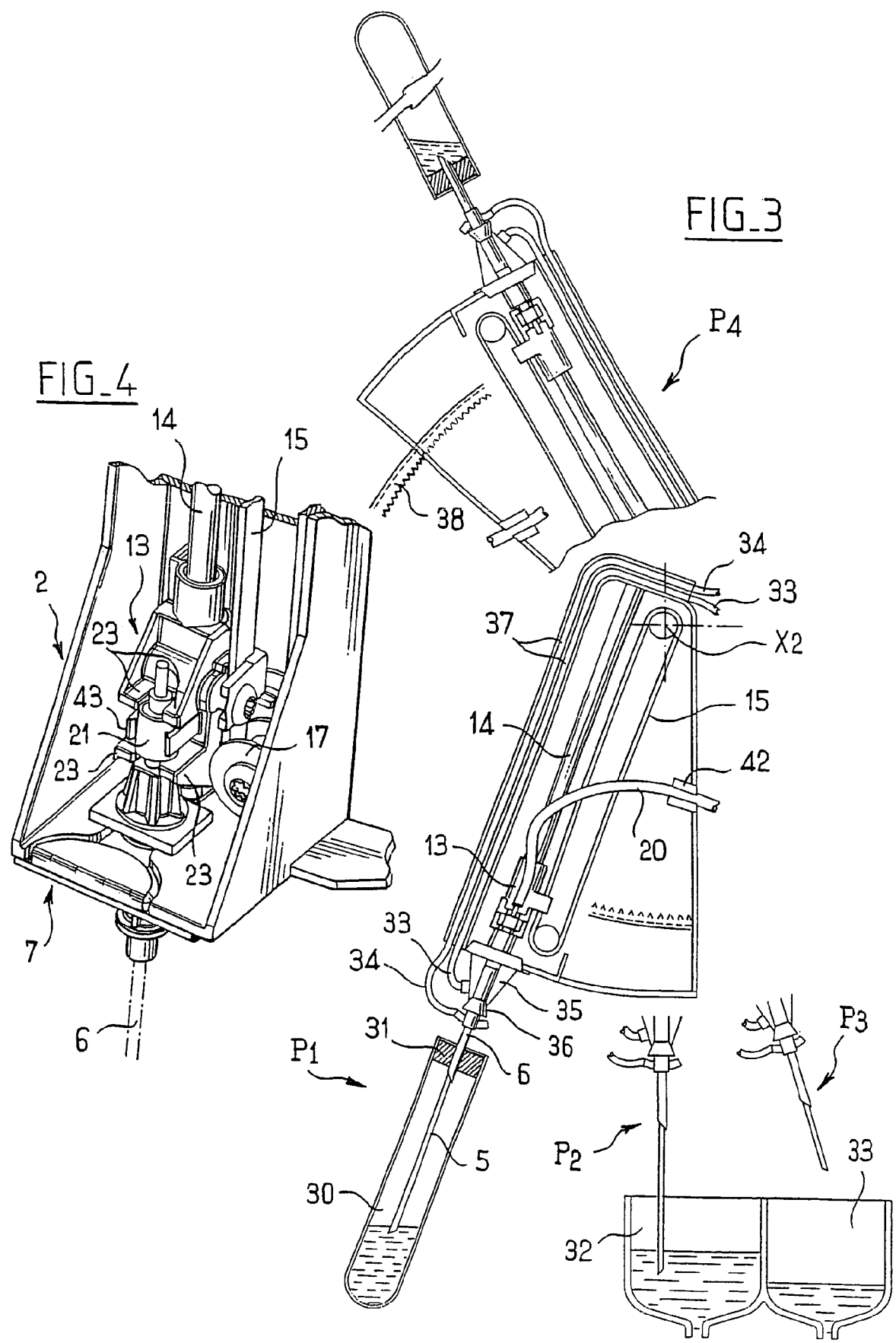

SAMPLING DEVICE AND METHOD FOR AN AUTOMATIC ANALYSER

The present invention relates to a device for taking samples in an automatic analysis apparatus, in particular for blood analysis. The present invention also relates to a method for sampling, a method suitable for use with a device according to the invention.

In particular in the field of haematology, there are numerous automatic apparatuses for taking blood samples and for analysis. The samples are very generally contained in a tube before being removed from there, at least partly, by the automatic apparatus which then analyzes them. The samples are removed with the help of a sampling needle which moves horizontally between the tube and one or more vessels serving for sample analysis, following possible dilution, vessels in which the sampling needle distributes the thus-removed sample.

A first type of horizontal movement of the needle is illustrated by document EP0468565. It involves horizontal linear translation of the needle. A second type of horizontal movement of the needle is illustrated by documents U.S. Pat. No. 4,166,094 and U.S. Pat. No. 4,022,067. In this second embodiment the needle is rotated about a vertical axis. In the two types, the needle is kept vertical during its movement. Such types of movement use mechanisms which are very bulky and thus not suitable for the realization of compact automatic apparatuses. Moreover, such mechanisms are often complex, having a large number of parts, and thus costly and fragile. These mechanisms can also be damaged by vapours or splashes from the vessels above and near to which they are located.

Moreover, tubing provided for cleaning the sampling needle must be able to move with the needle over the whole length of its movement. The large movement of the needle in the automatic apparatuses of the prior art necessitates the provision of long, and thus weakened, tubing. The same applies to the tubing connecting the needle to a sampling system, for example of the syringe type, forming a pump for drawing off the sample using the sampling needle.

In addition, given the position of the needle in a sampling device of the prior art, it can be difficult to replace it.

The sampling needle can twist, wear out or its seals leak.

The aim of the invention is to propose a sampling device which is simplified and less bulky. In such a device, the movement of the needle can advantageously be reduced, in particular to limit the length of the tubing. Another advantage of such a device can also be to make it easier to fit the needle into, and remove it from, the device.

The aim of the invention is also to propose a sampling method allowing at least one of the problems posed by the methods of the prior art to be solved, in particular the methods of moving the sampling needle.

According to the invention, a sampling method usable in an automatic analysis apparatus, said automatic apparatus including a needle for taking a sample to be analyzed, said sample being removed from a receptacle, for example a tube, is characterized in that the sampling needle is moved in rotation about an axis forming an angle with said sampling needle. This angle will preferably be chosen to be right-angled. To remove a sample the sampling needle can either be moved such that it points downwards, or be moved such that it points upwards.

If the receptacle is stopped with a bung, the receptacle can be directed such that the bung points downwards, the bung is pre-pierced with a pre-piercing needle by inserting it to the depth of said bung, then sliding the sampling needle inside the pre-piercing needle such that its tip is, for example, approximately flush with the tip of the pre-piercing needle, the sampling needle pointing upwards. This can allow approximately the whole sample contained in the receptacle to be removed, regardless in particular of the depth of the receptacle.

Advantageously, to give an operator easier access to the sampling needle, to remove the sample the sampling needle is moved such that it forms an angle with the vertical, in particular towards the front of the automatic apparatus.

After removing a sample, the needle is moved to at least one distribution position where the needle points downwards above a vessel.

According to the invention, a sampling device usable in an automatic apparatus, said device including a needle for taking a sample to be analyzed, said sample being removed from a receptacle, is characterized in that the sampling needle can move in rotation about an axis forming an angle, preferably approximately a right angle, with said sampling needle.

The device can comprise a rocker arm mobile about the axis, the sampling needle being mounted on this rocker arm. For immersion in the receptacle or a vessel, the needle will advantageously be mounted mobile in translation relative to the rocker arm describing a movement which moves it away from or towards the axis. The sampling needle can be mounted mobile in translation through a body fixed relative to the rocker arm. The body can advantageously be fixed on the rocker arm by self-locking which makes it easy to fit and remove the needle, in particular to change it.

The sampling needle and the body can be part of a double needle also including a pre-piercing needle, the sampling needle being mounted sliding in the pre-piercing needle, the pre-piercing needle being able to be mounted fixed on the body.

The device can include means for driving the sampling needle in translation relative to the rocker arm, said driving means comprising a carriage mobile in translation relative to the rocker arm and said needle being mounted by self-locking on the carriage. These driving means also include a belt stretched radially between a drive pulley and a loose pulley, one of the pulleys serving as a pivot on the rocker arm, the carriage being fixed on the belt and mobile in translation on a guide.

Other details and advantages of the invention will become clear from the following description, relating to non-limitative examples.

In the attached drawings:

FIG. 1 is a perspective three-quarters rear right-hand view of a sampling device according to the invention;

FIG. 2 is a view from the same perspective of a double needle for sampling as used in the device of FIG. 1;

FIG. 3 is a right-hand view schematically representing several different positions of the device of FIG. 1; and, FIG. 4 is a detail of FIG. 1 showing the fixing of the double needle on the rocker arm.

The front is defined as the side of the automatic apparatus facing an operator responsible for sampling, at the moment of sampling. The back is defined as the opposite side of the automatic apparatus. Right and left are defined as right and left of the operator taking a sample, i.e. looking from the front to the back.

FIG. 1 shows a sampling device 1. This device is part of an automatic apparatus for analyzing blood samples. To simplify the figures, the automatic apparatus is not represented in its entirety. The device comprises a rocker arm 2 and a double needle 3. The rocker arm 2 is mounted mobile in rotation about a horizontal rocker-arm axis X2, relative to a chassis 4 of the automatic sampling apparatus. The rocker arm is more or less four-cornered in shape.

The double needle 3 is shown on its own in FIG. 2. Such a needle comprises a sampling needle 5, a pre-piercing needle 6 and a body 7. Each of these needles is mainly composed of a cylindrical and hollow stem. The pre-piercing needle 6 is mounted fixed relative to the body 7. The sampling needle 5 is mounted sliding inside the pre-piercing needle 6. The body 7 is fixed on the rocker arm 2 such that the ends of the sampling needles 5 and pre-piercing needles 6 furthest from the rocker arm axis X2 constitute their respective tips 11, 12. The body is fixed on the rocker arm by means of fixing by locking 9.

The sampling device 1 also comprises means 8 for moving the sampling needle in translation relative to the rocker arm causing the sampling needle 5, in the example described, to slide in the pre-piercing needle 6. The sliding means 8 comprise a carriage 13, a guide 14 and a belt 15. The belt is mounted between a drive pulley 16 and a loose pulley 17. The drive pulley is coaxial with the rocker arm 2 axis and includes a shaft which serves as a pivot on the rocker arm; said drive pulley is driven by a first motor 18, fixed on the chassis 4. The loose pulley 17 is fixed near to the locking means of fixing 9 such that the belt extends approximately radially relative to the rocker arm axis X2. The guide 14 is cylindrical and extends parallel to the direction of the belt 15. The carriage is mounted sliding on the guide and fixed on the belt. A rail, hidden in the figures, serves as means of preventing the rotation of the carriage around the guide 14. In the embodiment described in the figures, this rail is a groove worked in the rocker. The carriage includes a tappet mounted sliding in this groove. Thus, the driving of the belt by the first motor 18 causes the rectilinear movement of the carriage on the guide.

Near its end 19, opposite its tip 11, the sampling needle includes a cylindrical boss 21 around the cylindrical hollow stem 22. As illustrated in particular in FIG. 4, the carriage 13 includes means 23, 43 for holding the sampling needle 5. These holding means comprise four fingers 23 extending approximately parallel to the rocker arm axis X2, and a clamp 43. On mounting the needle on the rocker arm, the body 7 of the double needle 3 is fixed on the rocker arm such that the needles 5, 6 extend parallel to the guide 14. Moreover, the boss is introduced parallel to the rocker arm axis such that two fingers 23 are arranged on either side of the stem 22 on a side of the boss closest to the end opposite the tip, two fingers 23 are arranged on either side of the stem 22 on a side of the boss closest to the tip 11 and the clamp 43 closes by locking around the boss 21. Thus, during its movement on the guide, the carriage 13 causes the sampling needle to slide in the pre-piercing needle and the body.

The sampling needle can thus assume a retracted position in which its tip is protected inside the pre-piercing needle. This position corresponds to a position of the carriage closest to the drive pulley 16.

The sampling needle can thus assume a fully-extended position outside the pre-piercing needle, a position in which its tip 11 is furthest away from the tip 12 of the pre-piercing needle.

This position corresponds to a position of the carriage closest to the loose pulley 17. It is this position that is shown in the figures.

The sampling needle can then also assume all the positions, more or less extended, between the two positions previously described.

The sampling device also includes means for pivoting the rocker arm 2 about its axis X2. Thus, a rack 24 is located chassis-side on the back of the rocker arm, i.e. on a surface opposite that carrying the belt, the guide and double needle. The rack 24 forms a circular arc around the rocker arm axis X2. A pinion 25, driven by a second motor 26, engages in the rack. Thus, the rotation of the second motor causes the rocker arm to pivot about its axis, and thus consequently the double needle to rock. The rack forms on the rocker arm 2 a groove 44 for guiding the rocker arm 2 on opposite surfaces of the pinion 25. The rack is arranged on the rocker arm in a part of the rocker arm away from the rocker arm axis X2. Thus, the force needed for the rocking movement is reduced and the second motor may be of reduced power and size.

We note that in the described example, the rocking and translation movements of the sampling needle are advantageously independent.

The opposite end 19 of the sampling needle 5 is connected via a sampling tube 20 (see FIG. 3) to a sampling system, not represented in the figures. It may be sufficient to use the capacity available in the sampling needle and optionally in the sampling tube to store the thus-removed sample there. The sampling tube 20 is held on the rocker arm 2 by a clip 42 such that the length of the tube between the clip and its connection to the sampling needle is sufficient to not hamper the movement of the carriage 13 along the guide 14.

The sampling device comprises two other tubes 33, 34 provided for rinsing the double needle. The first of these tubes is a tube 33 for rinsing the sampling needle 5. It serves to carry a rinsing product to a rinsing head 35 of the sampling needle. The second of these tubes is a tube 34 for rinsing the pre-piercing needle 36. It serves to carry a rinsing product to a rinsing head 36 of the pre-piercing needle 6. The rinsing heads are fixed relative to the rocker arm 2. Chutes 37 are formed on the rocker arm to guide the rinsing tubes there from the vicinity of the rinsing heads to the vicinity of the rocker arm axis X2. Thus, by bringing these tubes near to this axis, their movement is minimized, thus limiting their length, bulk and fragility.

The operation of the sampling device will now be described in more detail with reference to FIG. 3. FIG. 3 represents four possible positions of the double needle according to the position of the rocker arm about its axis. Each of these positions of the needle corresponds to a particular angle position of the rocker arm 2 about its axis X2.

A first position P1 is an actual sampling position. In this position, the sampling needle 5 serves to remove a blood sample from a tube 30. The tube is stopped with a bung 31. The bung must thus be pierced prior to sampling. For this, the sampling needle is placed in its position retracted inside the pre-piercing needle 6. The latter, stronger, allows the bung to be pierced without damaging the sampling needle. The pre-piercing needle, then being held through the bung, serves as a passage for the sampling needle through the bung. In this first position P1, the tips 11, 12 of the double needle are directed downward and slightly pivoted forwards such that they are easily accessible to the operator.

The removed sample is sucked up through the cylindrical hollow stem of the sampling needle. The sample is then divided into one or more vessels 32, 33 to be, for example, diluted or mixed with reagents with the aim of being analyzed. The automatic apparatus of FIG. 3 contains two vessels 32, 33. The vessels are aligned relative to the movement of the double needle such that for each vessel there is a position of this needle for which said needle overhangs said vessel. A second position is a distribution position P2 in which the sampling needle is directed with its tip pointing downwards, approximately vertically, above a first vessel 32. A third position is a distribution position P3 in which the sampling needle is directed with its tip pointing downwards, slightly further backwards than in the second position, above a second vessel 33. The second position is an intermediate position between the first position P1 and the third position P3.

The vessels may also serve to receive the soiled rinsing product after it has passed through the double needle. Instead of two rinsing tubes, a single tube or more than two tubes can be used according to their intended use. Thus these tubes 33, 34 can also be used when the double needle is above a vessel, to distribute a liquid into the vessel, either through or along one of the needles 5, 6.

In order to protect the rack from possible splashes from the vessels, a protective rim 40 is formed in a circular arc on the rocker arm beyond the rack relative to the rocker arm axis.

In distribution position P3, the sampling needle 5 is not fully extended, so that its tip 11 remains above the edges of the vessels 32, 33, in particular also during the pivoting of the rocker arm. Of course, as illustrated in position P2 of FIG. 3, the needle can also extend inside a vessel into a dilution liquid or reagent that it contains either to avoid spilling during the distribution of the sample, or to remove some of the contents of the vessel. Thus the first vessel can be used to dilute the blood sample, then the thus-diluted blood can be removed from the first bath to then be mixed with a reagent in the second vessel.

The three positions, P1, P2, P3 described above for the rocker arm are realized with an approximately forty-degree movement of the rocker arm about its axis. This corresponds approximately to the length of the arc formed by the rack 24 on the rocker arm in the configuration of FIG. 1. It may be possible that a position, P3 or beyond P3 relative with P2, i.e. toward rear, is provided to allow the vessels to be removed for changing or cleaning.

A fourth position P4, also represented in FIG. 3, can be reached, for example with an extended rack 38 allowing a pivoting of the lever about approximately 170 degrees. In this position, the rocker arm is pivoted beyond the first position P1 relative to the second position P2 and third position P3 such that it forms an angle of approximately 170 degrees with the third position P3. The tip of the needle points upwards and slightly pivoted forwards to be more easily accessible to the operator.

It will be noted that the sampling tubes are not all of the same depth. This can pose a problem if the sampling is automatic, i.e. if the operator places the tube into a support, and the automatic apparatus then automatically carries out by itself the pre-piercing, sampling and distribution operations. The sampling needle 5 can, in its fully-extended position, be provided to reach the very bottom of a tube that is not very deep.

Thus, as illustrated in the first position P1 in FIG. 3, it will be possible to remove the blood from the bottom of a tube 30 of greater depth only if the device includes, for example, means for adapting the extension of the sampling needle to the depth of the tube or means for positioning the tube relative to the needle according to the depth of the tube.

A sampling position in which the sampling needle points upwards, such as the fourth position P4 illustrated in FIG. 3, allows this problem to be solved when the tube used is stopped with a bung. Regardless of the depth of the tube, as the bung points downwards, the blood contained in the tube comes up against the bung. Thus the pre-piercing is carried out to the depth of the bung and the pre-piercing needle is kept there; it is then sufficient to position the tip 11 of the sampling needle 5 to collect the sample to be analyzed.

Of course the invention is not limited to the examples which have just been described, and numerous modifications can be made to these examples without departing from the scope of the invention.

In particular the number of vessels is not limited to two but can be more or less, as required.

Nor is the invention limited to blood analyses. It can be used for any type of sampling.

A rocker arm axis perpendicular to the extension direction and to the movement direction of the sampling needle, as illustrated in the figures, is generally preferable because it allows in particular the volume swept by the sampling device during its operation to be limited. Moreover, it allows a common axis to be more easily used for pivoting the rocker arm and for one of the pulleys. However, depending on the configuration of the automatic analysis apparatus, the rocker arm can form an angle other than a right angle with the sampling needle.

Other driving means for moving the sampling needle relative to the rocker arm can also be used, such as a rack or a screw/nut system. These means, more rigid than a belt, are preferable if the sampling needle is also used as a piercing needle for the bung.

Similarly, rather than a rack in a circular arc, means for swinging the rocker arm can comprise a screw/nut system, a belt or a cable. These means for swinging can be disposed to allow the rocker to make a complete rotation around its axis.

The angles formed between the different positions of the rocker arm about its axis can also differ from those described above.

The sampling device can also not include a pre-piercing needle. This can be the case when it is not provided that the tubes include a bung, which may have been removed in advance, or when the sampling needle is sufficiently solid to be used to pierce the bung.

The invention claimed is:

1. Sampling method that can be used in an automatic analysis apparatus, said automatic apparatus including a needle (5) for taking a sample to be analyzed, said sample being removed from a receptacle (30), said needle being fixed on a rocker mobile about an axis (X2) forming an angle with said sampling needle, characterized in that it comprises the following steps:
   rotating the sampling needle about the axis (X2)
   driving the sampling needle in translation relative to the rocker by driving means comprising a carriage (13) mobile in translation relative to the rocker and also a belt (15) stretched radially between a drive pulley (16) and a loose pulley (17), one of these pulleys serving as a pivot on the rocker, the carriage being fixed on the belt.

2. Method according to claim 1, characterized in that translation and rotation movement are independent.

3. Method according to claim 1, characterized in that, to remove the sample, the sampling needle is moved such that it points downwards.

4. Method according to claim 1, characterized in that, to remove the sample, the sampling needle is moved such that it forms an angle with the vertical.

5. Method according to claim 1, characterized in that, to remove the sample, the sampling needle is moved such that it points upwards.

6. Method according to claim 5, characterized in that if the receptacle is stopped with a bung (31), the receptacle is directed such that the bung points downwards, then the bung is pierced with a needle by inserting it at least to the depth of said bung.

7. Method according to claim 1, characterized in that, after having removed a sample, the needle is moved to a distribution position, (P2, P3) where the needle points downwards above a vessel (32, 33).

8. Method according to claim 7, characterized in that there is a position of the needle, in rotation about axis, so that the vessel can be removed from the apparatus.

9. Sampling device usable in an automatic analysis apparatus, said device including a needle (5) for taking a sample to be analyzed, said sampling needle being fixed on a rocker mobile about an axis (X2) forming an angle with said sampling needle, means (13-18) for driving the sampling needle in translation relative to the rocker, said driving means comprising a carriage (13) mobile in translation relative to the rocker and a belt (15) stretched radially between a drive pulley (16) and a loose pulley (17), one of these pulleys serving as a pivot on the rocker.

10. Device according to claim 9, characterized in that it comprises means so that the needle can be moved all around the axis.

11. Device according to claim 9, characterized in that the angle formed by the axis and the needle is a substantially right angle.

12. Device according to claim 9, characterized in that the sampling needle is mounted mobile in translation relative to the rocker, describing a movement which moves it away from or towards the axis.

13. Device according to claim 9, characterized in that it comprises means so that translation and rotation movements are independent.

14. Device according to claim 9, characterized in that the sampling needle is mounted by locking on the carriage.

15. Device according to claim 9, characterized in that the carriage is fixed on the belt and mobile in translation on a guide (14).

16. Device according to claim 9, characterized in that at least one needle (5, 6) includes a rinsing head (35, 36); in that it includes a tube (33, 34) to carry a rinsing product to said rinsing head, the rocker including at least one chute (37) to guide said tube from the vicinity of the rinsing head to the vicinity of the axis (X2).

17. Device according to claim 9, characterized in that the sampling needle is mounted mobile in translation through a body (7) fixed relative to the rocker.

18. Device according to claim 17, characterized in that it includes means (9) for fixing the body by locking on the rocker.

19. Device according to claim 17, characterized in that the sampling needle and the body form part of a double needle (3) also comprising a pre-piercing needle (6), the sampling needle being mounted sliding in the pre-piercing needle.

20. Device according to claim 19, characterized in that the pre-piercing needle is mounted fixed on the body.

21. Device according to claim 9, characterized in that the rocker includes means (24, 25) for pivoting the rocker about its axis.

22. Device according to claim 21, characterized in that the pivoting means include a rack (24) forming an arc about the axis (X2) and a pinion (25) engaging in the rack to drive the rocker in rotation about the axis.

23. Device according to claim 22, characterized in that the rack is provided on the rocker, in a part of the rocker distant from the axis.

24. Device according to claim 23, characterized in that the pivoting means comprise a belt or a cable or a screw/nut device.

* * * * *